(12) United States Patent
Shibata

(10) Patent No.: US 6,575,571 B2
(45) Date of Patent: Jun. 10, 2003

(54) FUNDUS CAMERA

(75) Inventor: Naohisa Shibata, Gamagori (JP)

(73) Assignee: Nidek Co., Ltd. (JP)

( * ) Notice: Subject to any disclaimer, the term of this patent is extended or adjusted under 35 U.S.C. 154(b) by 50 days.

(21) Appl. No.: 09/982,876

(22) Filed: Oct. 22, 2001

(65) Prior Publication Data

US 2002/0047989 A1 Apr. 25, 2002

(30) Foreign Application Priority Data

Oct. 20, 2000 (JP) ........................................ 2000-327024

(51) Int. Cl.[7] ................................................ A61B 3/14
(52) U.S. Cl. ...................................................... 351/206
(58) Field of Search ................................ 351/205, 206, 351/207, 208, 245, 246; 348/78

(56) References Cited

U.S. PATENT DOCUMENTS 3,915,564 A * 10/1975 Urban ........................ 351/206
5,589,899 A   12/1996 Maeda et al. ............... 351/245

FOREIGN PATENT DOCUMENTS

JP   HEI 7-178051      7/1995

* cited by examiner

Primary Examiner—George Manuel
(74) Attorney, Agent, or Firm—Rader, Fishman & Grauer PLLC

(57) ABSTRACT

A fundus camera in which control parts of its devices are simplified, thereby ensuring improved operability. The fundus camera is provided with a monitor, an observation device, a photographing device, a storage device, a mode selection device, and an input device. The observation device photographs an image of the fundus illuminated with infrared illumination light for observation, and display the image on the monitor. The photographing device has a photoelectric photographing element and a focusing lens movable in a direction of an optical axis to focus the image of the fundus on the photoelectric photographing element, and photograph an image of the fundus illuminated with illumination light for photographing. The storage device stores the image of the fundus photographed by the photographing device. The mode selection device selects one mode from a plurality of modes including at least one of a photographing mode for photographing the image of the fundus, a playback mode for playing back and displaying the photographed image of the fundus on the monitor, and a control mode for controlling the stored image of the fundus. The input device inputs a signal specific to the selected mode.

13 Claims, 5 Drawing Sheets

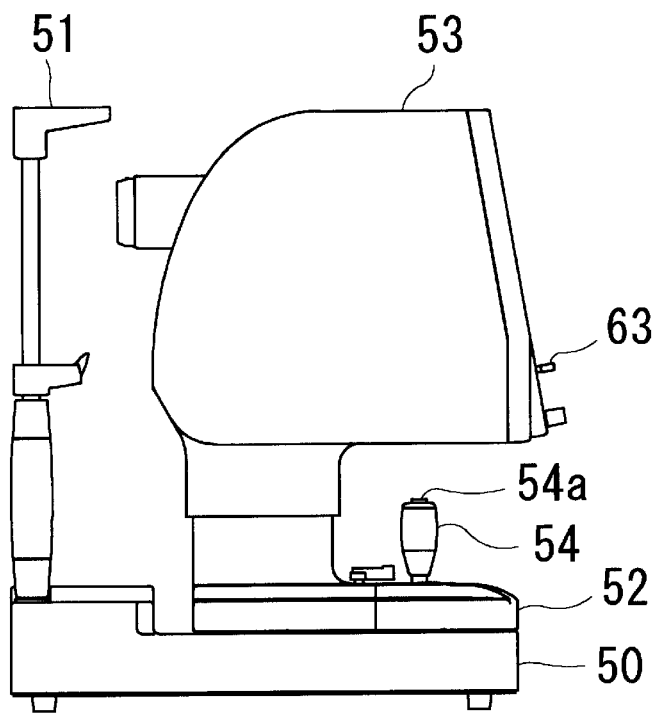
F I G. 1A
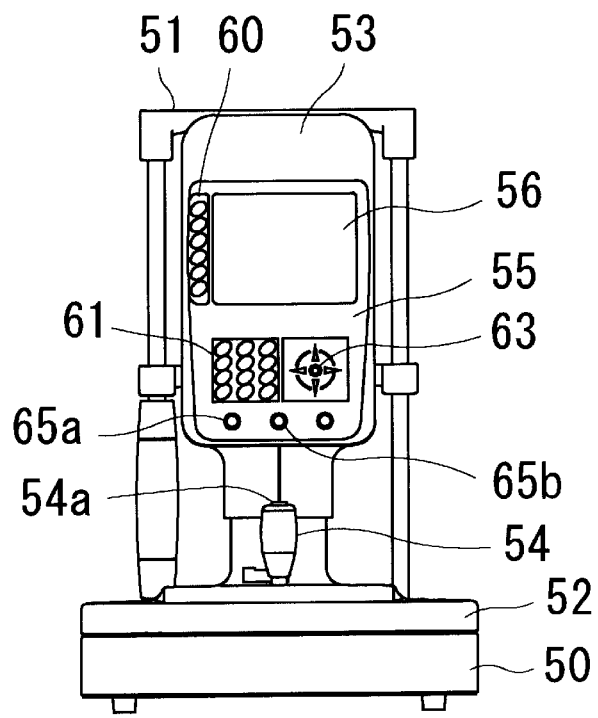
F I G. 1B

FUNDUS CAMERA

BACKGROUND OF THE INVENTION

1. Field of the Invention

The present invention relates to a fundus camera used in an ophthalmology clinic and the like.

2. Description of Related Art

Conventionally, a fundus camera for photographing a fundus to obtain its electronic image has been provided by attaching a digital camera to a camera mount for film photographing. A photographed image is observed, stored, and controlled by transferring its image data to an image control device such as a computer. In the image control device, manipulating an input device such as a keyboard or a pointer device provides relatively much freedom to zoom in/out on an image displayed on a monitor and to edit and control a stored image.

Under such a system, the fundus camera may well have a complicated configuration of devices as it is equipped with the image control device besides its main body. Therefore, it will be advantageous to design the system such that an operator may zoom in/out on and control the photographed image on a monitor for observation included in the fundus camera.

In this case, however, the fundus camera needs to be equipped with a multitude of control members for processing images as well as a variety of control members for adjusting photographing conditions (intensity of illumination light, movements of a focusing lens, and the like). This could complicate a configuration of control parts of the fundus camera. In addition, a multiplicity of the control members would degrade operability because it requires an operator to distinguish between the members to be operated for photographing and those to be operated for image playback viewing or image control.

SUMMARY OF THE INVENTION

The present invention has been made in view of the above circumstances and has an object to overcome the above problems and to provide a fundus camera intended for improving its operability by simplifying control parts of its devices.

To achieve the objects and in accordance with the purpose of the present invention, as embodied and broadly described herein, a fundus camera is provided with simplified control parts of its devices which improves operability. The fundus camera is provided with a monitor, observation means, photographing means, storage means, mode selection means, and input means. The observation means photographs an image of the fundus illuminated with infrared illumination light for observation, and displays the image on the monitor. The photographing means has a photoelectric photographing element and a focusing lens movable in a direction of an optical axis to focus the image of the fundus on the photoelectric photographing element, and photographs an image of the fundus illuminated with illumination light for photographing. The storage means stores the image of the fundus photographed by the photographing means therein. The mode selection means selects one mode from a plurality of modes including at least one of a photographing mode for photographing the image of the fundus, a playback mode for playing back and displaying the photographed image of the fundus on the monitor, and a control mode for controlling the stored image of the fundus. The input means inputs a signal specific to the selected mode.

In another aspect of the invention, the fundus camera is provided with a monitor, observation means, photographing means, moving means, storage means, mode selection means, and input means. The observation means photographs an image of the fundus illuminated with infrared illumination light for observation, and displays the image on the monitor. The photographing means has a photoelectric photographing element and a focusing lens movable in a direction of an optical axis to focus the image of the fundus on the photoelectric photographing element, and photographs an image of the fundus illuminated with illumination light for photographing. The moving means moves the focusing lens. The storage means stores the image of the fundus photographed by the photographing means therein. The mode selection means selects one mode from a plurality of modes including at least one of a photographing mode for photographing the image of the fundus, a playback mode for playing back and displaying the photographed image of the fundus on the monitor, and a control mode for controlling the stored image of the fundus. The input means inputs a signal for operating the moving means.

And yet, in another aspect of the invention, the fundus camera is provided with a monitor, an observation optical system, a photographing optical system, a storage part, a mode selection switch, a signal input unit, and a control part. The observation optical system has a photographing element for photographing an image of the fundus illuminated with infrared illumination light for observation. The photographing optical system has a photoelectric photographing element and a focusing lens movable in a direction of an optical axis to focus an image of the fundus illuminated with illumination light for photographing on the photographing element. The memory temporarily stores the photographed image of the fundus therein. The storage part stores the photographed fundus image therein. The mode selection switch for selecting one mode from a plurality of modes including at least one of a photographing mode for photographing the image of the fundus, a playback mode for playing back and displaying the temporarily stored image of the fundus on the monitor, and a control mode for controlling the stored image of the fundus. The signal input unit inputs a signal. The control part generates a control signal specific to an inputted signal based on the selected mode.

Additional objects and advantages of the invention are set forth in the following description, are obvious from the description, or may be learned by practicing the invention. The objects and advantages of the invention may be realized and attained by means of instrumentalities and combinations particularly pointed out in the claims.

BRIEF DESCRIPTION OF THE DRAWINGS

The accompanying drawings, which are incorporated in and constitute a part of this specification, illustrate embodiments of the present invention and, together with the description, serve to explain the objects, advantages and principles of the invention. In the drawings:

FIG. 1, consisting of FIGS. 1A and 1B, is an external view of a fundus camera according to the present invention;

DETAILED DESCRIPTION OF THE PREFERRED EMBODIMENTS

Figure 2:
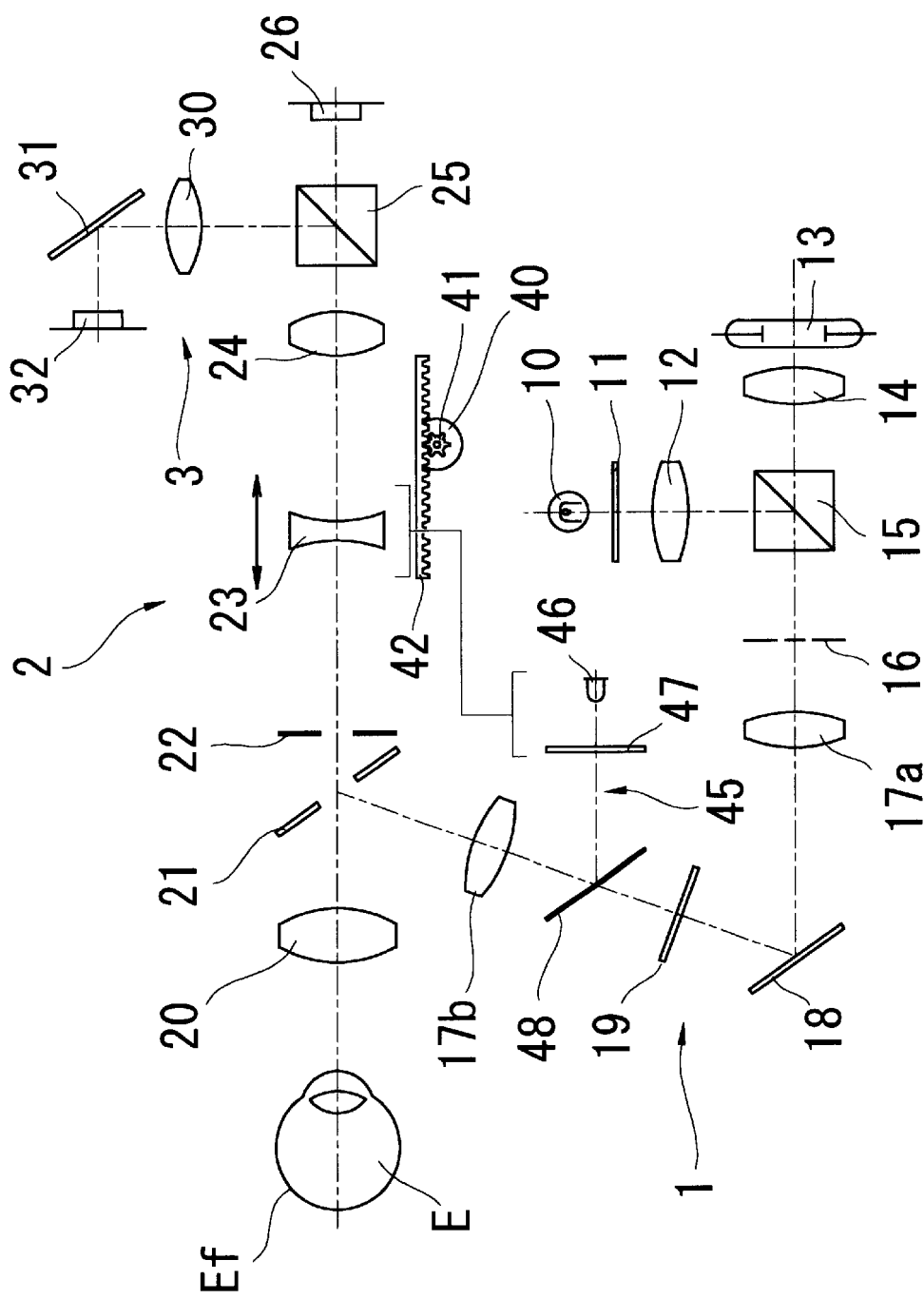
FIG. 2 is a view showing a schematic configuration of an optical system of the fundus camera shown in FIG. 1.

A detailed description of preferred embodiments of a fundus camera consistent with the present invention will now be given referring to the accompanying drawings. FIG. 1 is an external view of a fundus camera according to the present invention. FIG. 1A is its side view and FIG. 1B is its elevation as viewed from the side of an examiner.

A face support unit 51 is attached to a base 50 on the side of an examinee. A mobile base 52 movable in backward/forward and right/left directions is attached on the top surface of the base 50. A photographing part 53 containing an optical system for photographing is mounted on the mobile base 52 such that the photographing part 53 is movable in the up/down directions. A joystick 54 is provided to the mobile base 52 on the side of an examiner such that he may manipulate the joystick 54 to move the mobile base 52 in the forward/backward and right/left directions and to move the photographing part 53 in the up/down directions. A photographing switch 54a is provided at the top of the joystick 54.

A liquid crystal color monitor 56 and a control panel part 55 are arranged on the photographing part 53 on the side of the examiner. Provided on the control panel part 55 are a group of switches 60, a ten key switch 61, a control lever 63 used for many purposes, a rotation knob 65a for adjusting intensity of illumination light for observation, a rotation knob 65b for adjusting intensity of illumination light for photographing, and the like. The control lever 63 may be tilted either laterally or vertically (including midway between the two directions) to input control signals for each direction. In addition, it may be possible to design the control lever 63 to be tilted in eight directions.

FIG. 2 shows an optical system provided within the photographing part 53 of the present fundus camera, and the optical system comprises an illumination optical system 1, a photographing optical system 2, an observation optical system 3, and a focus target projection optical system 45.

<Illumination Optical System>

A halogen lamp 10 is an illumination light source for observation, and the light emitted from the lamp 10 is converted into infrared light by an infrared filter 11. The infrared light then passes through a condenser lens 12 and is reflected by a half mirror 15 to illuminate a ring slit 16. A flash lamp 13 is an illumination light source which emits visible light for photographing. The visible light emitted from the lamp 13 passes through a condenser lens 14, is transmitted by the half mirror 15 to be synthesized coaxially with the infrared light for observation, and then illuminates the ring slit 16.

Ring-slit light (the light from the ring slit 16) passes through a relay lens 17a, a mirror 18, a black-dot plate 19 with a small black dot on its center, a beam splitter 48, and a relay lens 17b, and forms an intermediate image in the vicinity of an aperture of an apertured mirror 21. The ring-slit light is then reflected by a peripheral surface of the mirror 21 to be made coaxial with an optical axis of the photographing optical system 2. Once the ring-slit light reflected by the apertured mirror 2 is converged by an objective lens 20 in the vicinity of the pupil of an eye E to be examined, the light is diffused to illuminate a fundus Ef of the eye E uniformly.

<Photographing Optical System>

The visible light reflected from the fundus Ef passes through the objective lens 20, the aperture of the apertured mirror 21, a photographing diaphragm 22, a focusing lens 23, an image forming lens 24, and a dichroic mirror 25. The visible light then enters a digital color CCD camera 26 for photographing a still-frame image, so that an image of the fundus Ef is formed on a photographing surface of the camera 26. The dichroic mirror 25 has a property of reflecting infrared light and transmitting visible light.

<Observation Optical System>

The observation optical system 3 shares optical parts ranging from the objective lens 20 to the dichroic mirror 25 with the photographing optical system 2, and the dichroic mirror 25 bifurcates an optical path of the infrared light. The infrared light reflected from the fundus Ef by the dichroic mirror 25 passes through a relay lens 30 to be reflected by a mirror 31. The infrared light then enters a CCD camera 32 for observation which has sensitivity to the infrared region, so that the image of the fundus Ef is formed on a photographing surface of the camera 32.

It should be noted that the focusing lens 23 is movable along an optical path shared between the photographing optical system 2 and the observation optical system 3. This accommodates a refractive error according to refractive power of the eye E. The focusing lens 23 is fixed on a rack 42 engaged with a pinion 41 fixed on a rotation shaft of a stepping motor 40. Rotation of the motor 40 moves the pinion 41 and the rack 42, which moves the focusing lens 23 along the optical axis to bring the image of the fundus Ef into focus on the photographing surfaces of the cameras 26 and 32.

<Focus Target Projection Optical System>

The focus target projection optical system 45 comprises a target plate 47, a LED 46 emitting infrared light for illumination, and the beam splitter 48. The target plate 47 and the LED 46 are designed to be movable in synchronization with the focusing lens 23. Once the light for projecting a target from the target plate 47 is reflected by the apertured mirror 21 to form an image on a plane conjugate with the fundus Ef, the light is projected onto the fundus Ef via the objective lens 20. Since the image of the focus target projected onto the fundus Ef is projected in infrared light, the light reflected from the image is reflected by the dichroic mirror 25 to be photographed by the camera 32 together with the image of the fundus Ef.

Figure 3:
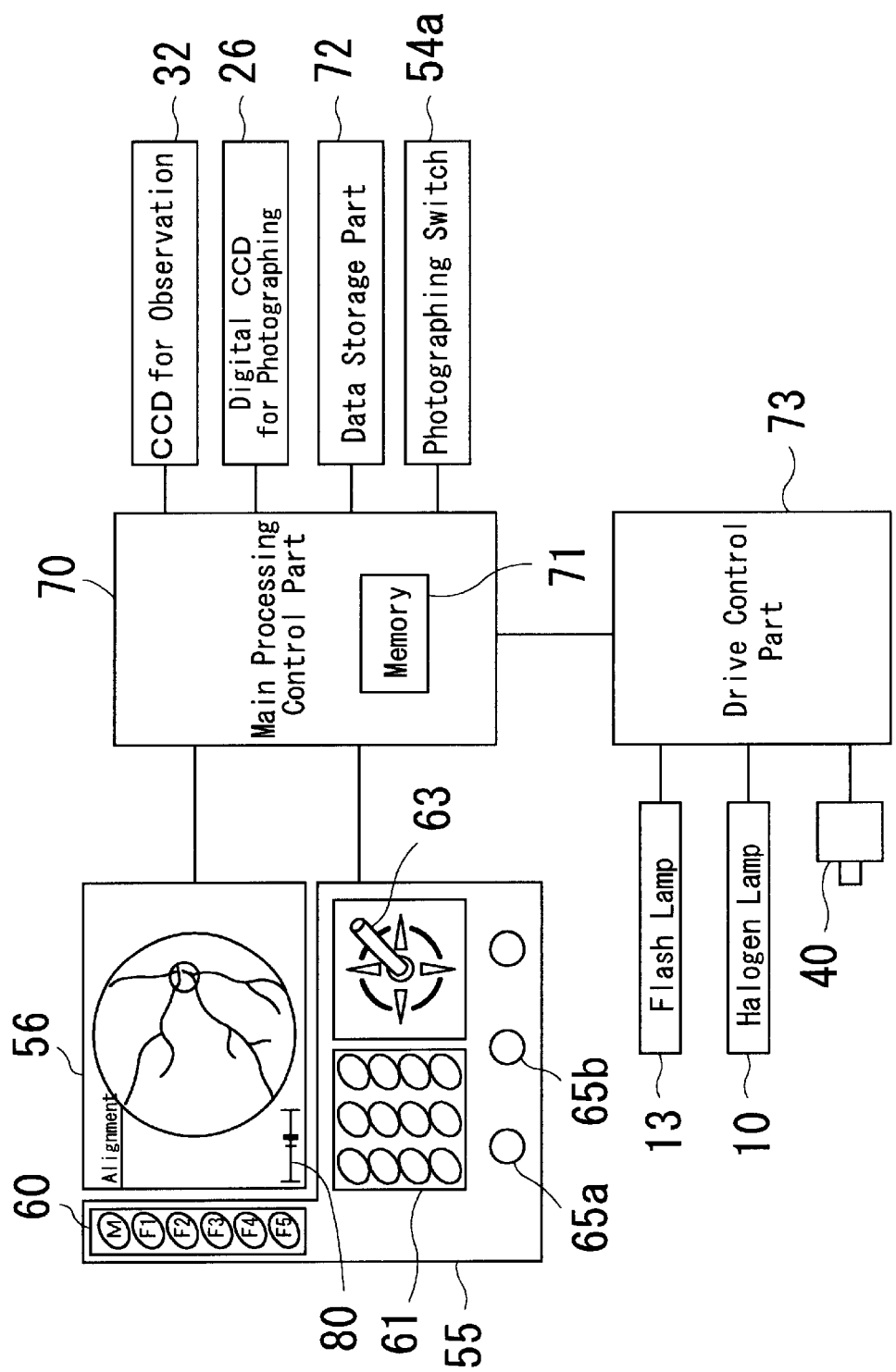
FIG. 3 is a schematic block diagram of a control system of the fundus camera.

FIG. 3 is a block diagram of a control system. The respective outputs from the cameras 32 and 26 are inputted to a main processing control part 70 connected to a monitor 56, so that moving images to be observed from the camera 32 are displayed on the monitor 56. A still-frame image from the camera 26 is stored in memory 71 for temporary storage included in the main processing control part 70, and the image stored in the memory 71 is displayed on the monitor 56. Connected to the main processing control part 70 are the control switches 60 and 61 on the control panel 55, a data storage part 72, a drive control part 73 which controls each driving part of the optical system, and the photographing switch 54a. The drive control part 73 receives signals for driving each of the driving parts of the optical system so as to control actuation of the motor 40, the flash lamp 13, and the like.

Next, description will now be given to operations performed in the above-described configuration.

At the time of photographing, among the switches 60, a mode switch 60a is used to select a photographing mode. A state of operational mode in the devices is indicated on an upper left corner of the screen on the monitor 56. When the photographing mode is selected, the halogen lamp 10 is turned on to illuminate the eye E in infrared light. An image of the eye E illuminated in infrared light is formed in the camera 32 to be displayed on the monitor 56. An examiner observes the display on the monitor 56 and performs alignment of the photographing part 53 with respect to the eye E. Besides, he makes the eye E gaze at an unillustrated fixation target to guide its line of sight.

In the photographing mode, the control lever 63 is set to function as a control switch for moving the focusing lens 23. When the control lever 63 is tilted to either the right or left, its control signals are inputted to the drive control part 73 via the main processing control part 70. The drive control part 73 controls the actuation of the motor 40 such that the focusing lens 23 is moved toward the eye E when the control lever 63 is tilted to the left and such that the same lens is moved away from the eye E when the control lever 63 is tilted to the right. By manipulating the control lever 63 to move the focusing lens 23, the examiner can achieve proper focus with respect to the fundus Ef. A state of movement of the focusing lens 23 is indicated by an indicator 80 appearing in a lower left corner of an alignment screen displayed on the monitor 56 (see FIG. 3).

The alignment performed by moving the focusing lens 23 utilizes the image of the focus target (an image of the target plate 47) photographed by the camera 32 together with the image of the fundus Ef. While the examiner observes on the monitor 56 the images of the fundus Ef and of the focus target photographed by the camera 32, he manipulates the control lever 63 to bring the focus target image into focus. A state of focus is detected as the examiner observes the focus target image on the monitor 56. Alternatively, it may be possible that the main processing control part 70 conducts image processing on image signals from the camera 32 so as to detect the focus target image, and that the examiner is informed of the focus state based on information about the detected image.

After correct focus has been obtained on a desired part on the fundus Ef to be photographed, the photographing switch 54a is depressed to input its signals to the drive control part 73 via the main processing control part 70. Consequently, the drive control part 73 lights the flash lamp 13 to illuminate the fundus Ef in visible light. The visible light reflected from the fundus Ef passes through the optical path of the photographing optical system 2, and forms an image in the camera 26 whereby an image of the fundus Ef is photographed. The obtained fundus image is stored in the memory 71 for temporary storage.

Figure 4:
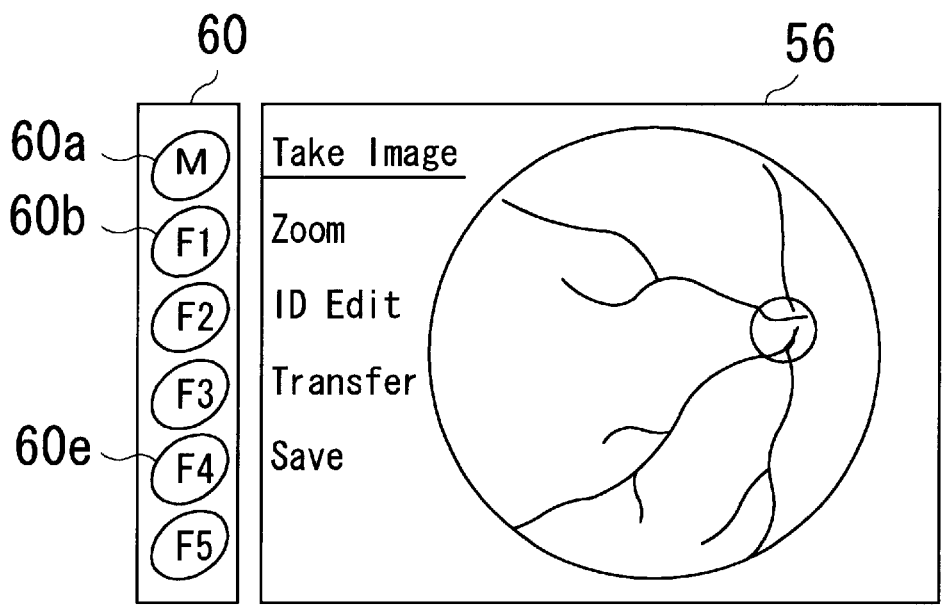
FIG. 4 is a view showing an example of a screen in an image playback viewing mode.
Figure 5:
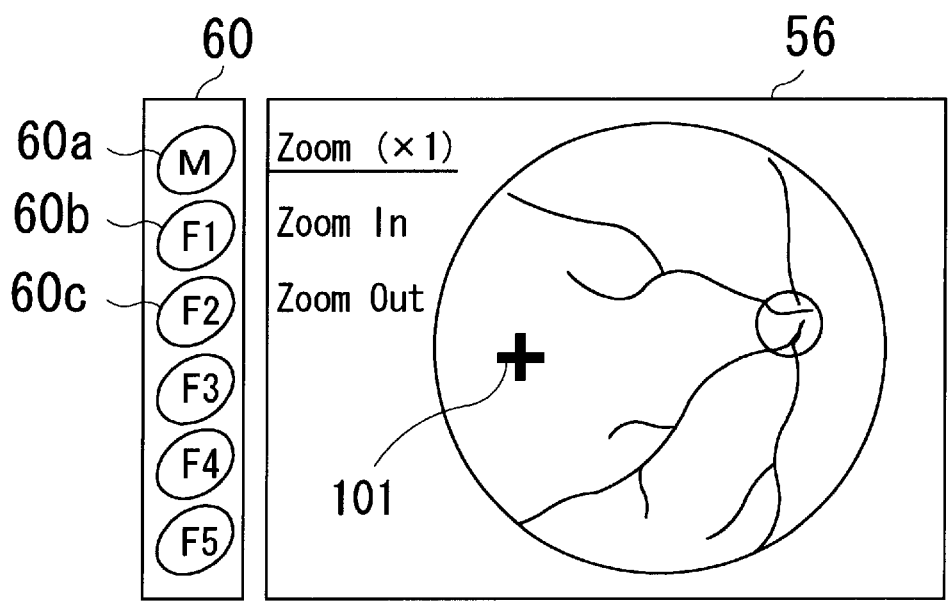
FIG. 5 is a view showing an example of a zoom screen.

After the photographed image (the fundus image) has been obtained, the main processing control part 70 exercises control such that the photographing mode is automatically shifted to an image playback-viewing mode. As a result, the still-frame fundus image stored in the memory 71 is displayed on the monitor 56. FIG. 4 is an example of a screen at this point, which shows a main screen in the image playback-viewing mode. With this screen on display, the F1 switch 60b is depressed to shift the screen on the monitor 56 to a zoom screen in a zoom playback-viewing mode for zooming in/out on a photographed image. FIG. 5 is an example of the zoom screen, on which the main processing control part 70 exercises control so as to bring a cursor 101 into view for specifying a reference position for zooming in/out (i.e. a center of zoom). With the zoom screen on display, the control lever 63 is set to function as a control switch for shifting the cursor 101 on the screen. That is, when the control lever 63 is tilted either vertically or laterally, its control signals are inputted to the main processing control part 70, which then controls the cursor 101 such that its position displayed on the monitor 56 shifts with reference to the inputted control signals.

The examiner thus specifies the reference position in the image on which to zoom in/out. Next, when he depresses the F1 switch 60b shown in FIG. 5, which functions as a switch for zooming in on an image in the zoom playback viewing mode, image data are computed to scale up its display at 200 percent with reference to the position of the cursor 101. Consequently, the image thus enlarged is displayed on the monitor 56. To reduce the image having been enlarged, he depresses a F2 switch 60c, which functions as a switch for zooming out on an image in the zoom playback-viewing mode. This time, the image data are computed to scale down the display by one half with reference to the position of the cursor 101. Consequently, the image thus reduced is displayed on the monitor 56.

With the zoom screen on display, the mode switch 60a is depressed to shift the screen on the monitor 56 to the main screen shown in FIG. 4. To save the photographed image in the data storage part 72, with the main screen on display, a F4 switch 60e is depressed to call up a screen for "Save" (not illustrated), where a file name in numerals is entered through a ten key, and the image data stored in the memory 71 is then saved into the data storage part 72.

Figure 6:
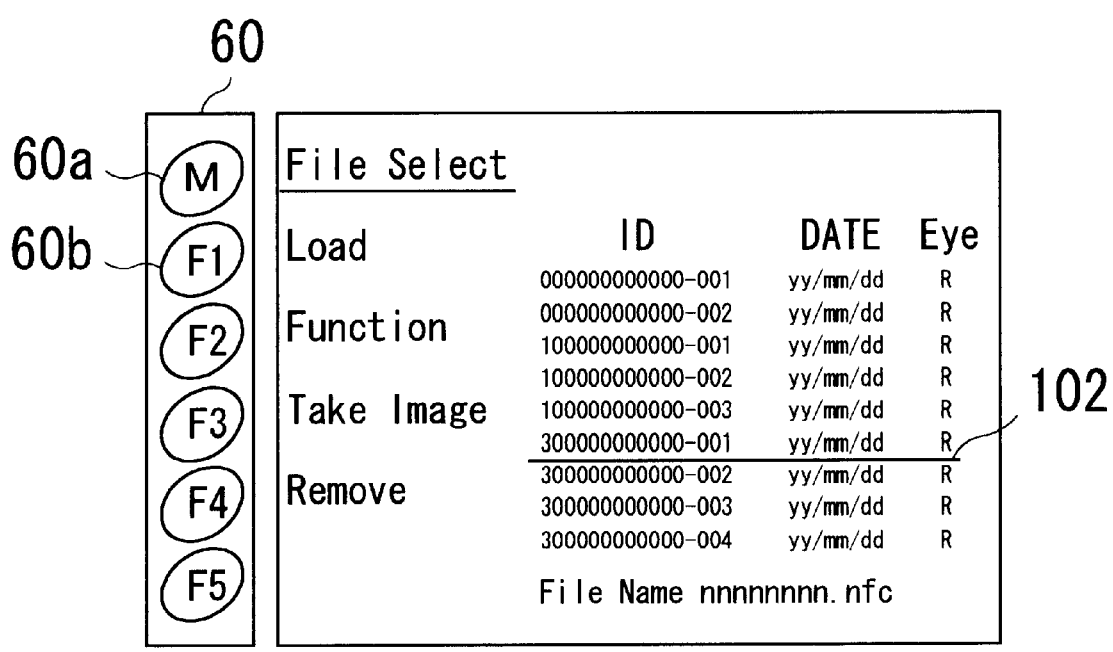
FIG. 6 is a view showing an example of a screen in an image data control mode.

FIG. 6 is an example of a screen in an image data control mode for displaying and editing plural sets of image data stored in the data storage part 72. The mode switch 60a is also used to select this mode. On the monitor 56, the screen appears with a list of ID numbers and a line cursor 102. The ID numbers in a one-to-one correspondence with the sets of image data stored in the data storage part 72, and the line cursor 102 is used to select any of the sets of image data. It should be noted that, in advance of photographing, a new ID number and its last few digit number are entered in an ID number entry screen, so that these numbers are stored and controlled associated with the corresponding photographed image. In addition, while the screen display is in this mode, the control lever 63 functions as a control switch to input signals for control information, for example, selecting a set of data on an image to be played back, or a screen jump.

When the control lever 63 is tilted either up or down, control signals for the direction are inputted to the main processing control unit 70 so as to control the cursor 102 to be shifted up and down on the ID list of the image data according to the direction in which the lever 63 is tilted. After one of the sets of the image data has been selected by shifting the cursor 102, the selected image is loaded from the data storage part 72 by depressing the F1 switch 60b. The main processing control part 70 then exercises control to shift the screen display on the monitor 56 to display a played back image so that the loaded image is displayed thereon (not illustrated). The screen for image playback may be shifted to the screen for zoom display by depressing the F1 switch 60b as is in FIG. 4.

In the image data control mode shown in FIG. 6, the control lever 63 is tilted to the right to put the list of the image data forward by one screen, and the same lever is tilted to the left to put the same list backward by one screen. This step allows the examiner to select a screen of the list containing desired image data.

As described up to this point, according to the present embodiment, a signal from the control lever 63 in the photographing mode is intended as a signal for moving the focusing lens 23. However, the control lever 63 may be intended to function for adjusting the intensity of light from the halogen lamp 10 for observation, or from the flash lamp 13 for photographing, or from both. Since the control lever 63 is capable of receiving control signals for the four directions of up/down and right/left, for example, the right/ left directions may be intended to adjust the intensity of light for observation, and the up/down directions may be intended to adjust the intensity of light for photographing. The light intensity of each light source is controlled by the drive control part 73.

In addition, in the image playback-viewing mode, the control lever 63 may be used zoom in/out on a photographed image. Instead of the control lever, it may be possible to use another signal input means such as a track boll or a switch. Moreover, a plurality of monitors may be provided to display an observed image, a photographed image, a control screen, and the like individually thereon.

Having fully been described, according to the present invention, the control parts of the devices may be simplified, thereby ensuring improved operability.

The foregoing description of the preferred embodiments of the invention has been presented for purposes of illustration and description. It is not intended to be exhaustive or to limit the invention to the precise form disclosed, and modifications and variations are possible in the light of the above teachings or may be acquired from practice of the invention. The embodiments chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. A fundus camera for photographing a fundus of an eye to be examined comprising:
   (a) a monitor;
   (b) observation means for photographing an image of the fundus illuminated with infrared illumination light for observation and for displaying the image on the monitor;
   (c) photographing means for photographing an image of the fundus illuminated with illumination light for photographing, the photographing means having a photoelectric photographing element and a focusing lens movable in a direction of an optical axis to focus the image of the fundus on the photoelectric photographing element;
   (d) storage means for storing the image of the fundus photographed by the photographing means therein;
   (e) mode selection means for selecting one mode from a plurality of modes, the modes including at least one of a photographing mode for photographing the image of the fundus, a playback mode for playing back and displaying the photographed image of the fundus on the monitor, and a control mode for controlling the stored image of the fundus; and
   (f) input means for inputting a signal specific to the selected mode.

2. The fundus camera according to claim 1, further comprising moving means for moving the focusing lens,
   wherein the input means inputs a signal for operating the moving means in the photographing mode.

3. The fundus camera according to claim 1, wherein:
   a) the observation means has an illumination light source for observation of which light intensity is variable;
   b) the photographing means has an illumination light source for photographing of which light intensity is variable; and
   c) the input means inputs a signal for changing the light intensity of at least one of the illumination light source for observation and the illumination light source for photographing in the photographing mode.

4. The fundus camera according to claim 1, further comprising zoom means for zooming in or out on the fundus image played back and displayed on the monitor while a cursor superimposed on the image is displayed in a center of the image,
   wherein the input means inputs a signal for shifting a position of the displayed cursor in the playback mode.

5. The fundus camera according to claim 1, further comprising zoom means for zooming in or out on the fundus image played back and displayed on the monitor,
   wherein the input means inputs a signal for zooming in or out on the fundus image in the playback mode.

6. The fundus camera according to claim 1, further comprising control screen display means for displaying a data control screen on the monitor,
   wherein the input means inputs a signal for giving a predetermined instruction to the data control screen in the control mode.

7. A fundus camera for photographing a fundus of an eye to be examined comprising:
   (a) a monitor;
   (b) observation means for photographing an image of the fundus illuminated with infrared illumination light for observation and for displaying the image on the monitor;
   (c) photographing means for photographing an image of the fundus illuminated with illumination light for photographing, the photographing means having a photoelectric photographing element and a focusing lens movable in a direction of an optical axis to focus the image of the fundus on the photoelectric photographing element;
   (d) moving means for moving the focusing lens;
   (e) storage means for storing the image of the fundus photographed by the photographing means therein;
   (f) mode selection means for selecting one mode from a plurality of modes, the modes including at least one of a photographing mode for photographing the image of the fundus, a playback mode for playing back and displaying the photographed image of the fundus on the monitor, and a control mode for controlling the stored image of the fundus; and
   (g) input means for inputting a signal for operating the moving means.

8. The fundus camera according to claim 7, further comprising detection means for detecting a state of focus by projecting a target for focus detection onto the fundus.

9. A fundus camera for photographing a fundus of an eye to be examined comprising:
   (a) a monitor;
   (b) an observation optical system having a photographing element for photographing an image of the fundus illuminated with infrared illumination light for observation;
   (c) a photographing optical system having a photoelectric photographing element and a focusing lens movable in a direction of an optical axis to focus an image of the fundus illuminated with illumination light for photographing on the photographing element;
   (d) a storage part for storing the photographed fundus image therein;
   (e) a mode selection switch for selecting one mode from a plurality of modes, the modes including at least one of a photographing mode for photographing the image of the fundus, a playback mode for playing back and displaying the photographed image of the fundus on the monitor, and a control mode for controlling the stored image of the fundus;

(f) a signal input unit; and (g) a control part which generates a control signal specific to an inputted signal based on the selected mode.

10. The fundus camera according to claim 9, further comprising a moving unit which moves the focusing lens, wherein the control part generates a control signal to the moving unit in accordance with the inputted signal in the photographing mode.

11. The fundus camera according to claim 9, wherein:

(a) the observation optical system has an illumination light source for observation of which light intensity is variable;

(b) the photographing optical system has an illumination light source for photographing of which light intensity is variable; and (c) the control part generates a control signal to at least one of the illumination light source for observation and the illumination light source for photographing in accordance with the inputted signal in the photographing mode.

12. The fundus camera according to claim 9, wherein the control part generates a control signal to the monitor in accordance with the inputted signal in the playback mode.

13. The fundus camera according to claim 9, wherein the control part generates a control signal to the storage part in accordance with the inputted signal in the control mode.

* * * * *